(12) United States Patent
Wu et al.

(10) Patent No.: US 7,386,093 B2
(45) Date of Patent: Jun. 10, 2008

(54) METHOD AND AN APPARATUS FOR LIQUID SAFETY-DETECTION WITH A RADIATION SOURCE

(75) Inventors: Wanlong Wu, Beijing (CN); Haifeng Hu, Beijing (CN); Yuanjing Li, Beijing (CN); Zhiqiang Chen, Beijing (CN); Kejun Kang, Beijing (CN); Yulan Li, Beijing (CN); Li Zhang, Beijing (CN); Yinong Liu, Beijing (CN); Xuewu Wang, Beijing (CN); Bin Sang, Beijing (CN); Hailin Wang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 95 days.

(21) Appl. No.: 11/285,398

(22) Filed: Nov. 23, 2005

(65) Prior Publication Data

US 2006/0115044 A1 Jun. 1, 2006

(30) Foreign Application Priority Data

Nov. 26, 2004 (CN) .................... 2004 1 0009896

(51) Int. Cl.
*G01N 23/083* (2006.01)
*G01N 23/087* (2006.01)
(52) U.S. Cl. .................... 378/57; 378/53; 378/98.9
(58) Field of Classification Search ............. 378/51, 378/52, 53, 54, 55, 56, 57, 98.9, 5, 9
See application file for complete search history.

(56) References Cited

U.S. PATENT DOCUMENTS 4,090,074 A * 5/1978 Watt et al. ................... 378/88

(Continued)

FOREIGN PATENT DOCUMENTS

CN 2314370 Y 4/1999

(Continued)

OTHER PUBLICATIONS

Police Technology, No. 1,2000, Yang, Lirui "Detecting function for explosives or drugs of dual energy x-rays security inspection device", pp. 8-10.

(Continued)

*Primary Examiner*—Allen C. Ho
(74) *Attorney, Agent, or Firm*—Berenato, White & Stavish

(57) ABSTRACT

A method and an apparatus for liquid safety-detection with a radiation source relate to a radiation detecting technology. The main steps of the method of the invention are: conveying an article to be detected into an operation zone within a radiation shield; allowing a ray beam to be emitted from the radiation source, to pass through the article to be detected, and to be received by a detector; transmitting the received ray signal to a data collector by the detector; amplifying and forming the ray signal, and transmitting such data to a data processing computer by the data collector, and transmitting a data collected by thickness measuring probing heads to the data processing computer by the same; and processing a data from the data collector and a data from the thickness measuring probing heads to derive the density and atomic number of the detected liquid, comparing a result with the densities and atomic numbers of dangerous articles in a existing database, and displaying the detected information of the detected article, by the data processing computer. Comparing to the prior art, the invention is not subjected to the affection of the outside package of an article and has great anti-interference, and has the features of small volume, high accuracy of detection, easy shielding, and high use safety and reliability.

6 Claims, 2 Drawing Sheets

U.S. PATENT DOCUMENTS

| | | | |
|---|---|---|---|
| 5,132,998 A | 7/1992 | Tsutsui et al. | |
| 5,400,381 A * | 3/1995 | Steude et al. | 378/57 |
| 5,597,473 A | 1/1997 | Hambitzer et al. | |
| 5,604,784 A * | 2/1997 | Widlicka et al. | 378/203 |
| 5,692,029 A * | 11/1997 | Husseiny et al. | 378/88 |
| 5,982,484 A | 11/1999 | Clarke et al. | |
| 6,052,611 A * | 4/2000 | Yanof et al. | 600/429 |
| 6,173,033 B1 * | 1/2001 | Klingenbeck-Regn et al. | 378/20 |
| 6,198,795 B1 * | 3/2001 | Naumann et al. | 378/57 |
| 6,320,936 B1 * | 11/2001 | Holland et al. | 378/140 |
| 6,370,223 B1 * | 4/2002 | Gleason et al. | 378/58 |
| 6,563,906 B2 * | 5/2003 | Hussein et al. | 378/89 |
| 6,597,759 B2 * | 7/2003 | Mazess et al. | 378/53 |
| 6,600,805 B2 * | 7/2003 | Hansen | 378/53 |
| 6,987,833 B2 * | 1/2006 | Du et al. | 378/98.9 |
| 6,990,171 B2 * | 1/2006 | Toth et al. | 378/16 |
| 7,050,533 B2 * | 5/2006 | Heismann et al. | 378/53 |
| 7,149,278 B2 * | 12/2006 | Arenson et al. | 378/19 |
| 7,206,376 B2 * | 4/2007 | Fitzgerald | 378/54 |
| 2006/0133566 A1 * | 6/2006 | Li et al. | 378/57 |
| 2006/0159220 A1 * | 7/2006 | Heuscher | 378/9 |
| 2006/0239402 A1 * | 10/2006 | Hu et al. | 378/54 |

FOREIGN PATENT DOCUMENTS

| | | |
|---|---|---|
| EP | 1 380 834 A1 | 1/2004 |
| WO | WO 02/31536 A2 | 4/2002 |

OTHER PUBLICATIONS

Police Technology, No. 4, 2001, Yang, Lirui "Automatic x-rays detecting system for explosives", pp. 22-24.

* cited by examiner

METHOD AND AN APPARATUS FOR LIQUID SAFETY-DETECTION WITH A RADIATION SOURCE

CROSS REFERENCE TO RELATED APPLICATION

The present application claims the benefits of the Chinese Application No. 200410009896.6 filed with the Chinese Patent Office on Nov. 26, 2004, the entirety of which is incorporated into this application by reference.

FIELD OF THE INVENTION

The invention relates to a radiation detecting technology field, and in particular, to a method and an apparatus for liquid safety-detection with a radiation source.

DESCRIPTION OF THE PRIOR ART

In a safety detection system of civil aviation, it is required that the liquid articles taken with passengers are examined without opening them. The detection methods used in the prior art mainly comprise a chemical method, an electromagnetic method and a neutron detection method. The chemical method is again classified into an odor identification method and an ion scanning explosive detection method and the like, which methods often fail to accomplish detection in practical applications because the liquid articles are sealed and packaged, and further the chemical method suffers from strong sensitivity and high error detection ratio. The electromagnetic detection method is prone to be electromagnetically interfered due to its weak signal, and can not be used to detect liquid articles with metal packages. The use of the neutron detection method will cause residual radiation remained in the detected liquid because of the "neutron activation", and the radiation shielding is complicate and has poor stability, great cover area and high investment, so that the method is not suitable for large scale applications in the safety detection system of civil aviation. In the existing X-ray scanning detection systems, the X-ray passed through a detected article is detected by a detector to reflect the density distribution in the detected article depending on the intensity variation of the X-ray, and the intensity of the X-ray is converted into an image grey scale so that the perspective image of the detected article is obtained. Such X-ray scanning detection method, which forms image by identifying the density information and shape information of the detected article, fails to accomplish image formation detection for a liquid article with uniform density distribution.

SUMMARY OF THE INVENTION

In order to overcome the defects existing in the prior art, the purpose of the invention is to provide a method and an apparatus for liquid safety-detection with a radiation source. The method can make safety detection for a liquid article without removing its package, and the detection result is not affected by the material quality of the package; and the apparatus of the invention has advantages of small covering area, high accuracy, high safety and reliability, and easy protection. The method and the apparatus are applicable to safety detection systems of civil aviation and other important sites.

In order to achieve the above-mentioned purposes of the invention, the technical solution of the invention can be realized in the following manner:

A method for safety-detecting a liquid with a radiation source comprises using the radiation source, a shield type collimator, a post collimator, a detector, a data collector, a data processing computer, thickness measuring probing heads and a radiation shield; and has the main steps of:

a) conveying an article to be detected into an operation zone within the radiation shield by a conveying mechanism;

b) allowing a ray beam to be emitted from the radiation source located in the shield type collimator, to pass through the article to be detected, then to pass a post collimator, and to be received by the detector facing the ray beam;

c) transmitting a data of a signal of a received ray beam to the data collector, by the detector;

d) amplifying and forming the data of the signal of the received ray beam and transmitting such data to the data processing computer by the data collector, and transmitting a data collected by the thickness measuring probing heads mounted on both sides of the conveying mechanism to the data processing computer by the same; and e) processing a data from the data collector and a data from the thickness measuring probing heads and accomplishing an energy spectrum analysis of a penetrated ray beam of the detected article to derive the liquid density and atomic number of the detected article, comparing a result with the densities and atomic numbers of dangerous articles in a existing database, and then visually displays a detected information of the detected article, by the data processing computer.

An embodiment form of an apparatus realizing the above described method for liquid safety-detection with a radiation source comprises a radiation shield, and a radiation source for emitting a ray beam, a shield type collimator, a conveying mechanism, thickness measuring probing heads, a post collimator and a detector, which are located in the radiation shield. The embodiment form further comprises a data collector having an amplifying and forming circuit, and a data processing computer provided with a database having substance densities and atomic numbers of dangerous liquids and with an energy spectrum analyzing software for carrying out an energy spectrum analysis of the ray beam emitted from the radiation source and penetrated through a liquid article to be detected, which data collector and data processing computer are located outside of the radiation shield. The structure features of the embodiment form are that said radiation source is located in the shield type collimator and that the shield type collimator is located on one side of the conveying mechanism on which an article to be detected can be placed. On the other side of the conveying mechanism successively mounted are the post collimator and the detector, to make the ray beam emitted from the radiation source face the post collimator and the detector after passing through the shield type collimator. The signal output line of the detector is connected with the data collector, and the data output lines of the data collector and the thickness measuring probing heads mounted on both sides of the conveying mechanism are all connected with the data processing computer.

In the above described apparatus, said radiation source may be an isotope of a radiation source having either a single energy level or multiple energy levels, and may be an X-ray machine or a linear electron accelerator as well.

Another embodiment form of an apparatus realizing the above described method for liquid safety-detection with a radiation source comprises a radiation shield, and double radiation sources each for emitting a ray beam, shield type collimators, a conveying mechanism, thickness measuring probing heads, post collimators and detectors, which are located in the radiation shield. The embodiment form further comprises a data collector having an amplifying and forming circuit, and a data processing computer provided with a database having substance densities and atomic numbers of dangerous liquids and with a liquid energy spectrum analyzing software for carrying out an energy spectrum analysis of the ray beam emitted from the radiation sources and penetrated through a liquid article to be detected, which data collector and data processing computer are located outside of the radiation shield. The structure features of the embodiment form are that said double radiation sources are composed of a low energy radiation source and a high energy radiation source which are respectively located in the shield type collimators. Each shield type collimator is located on one side of the conveying mechanism on which an article to be detected can be placed, and on the other side of the conveying mechanism successively mounted are the post collimators and a low energy detector, a high energy detector, to make the ray beam emitted from the low energy radiation source face the post collimator and the low energy detector after passing through the shield type collimator, and the ray beam emitted from the high energy radiation source face the post collimator and the high energy detector after passing through the shield type collimator. The data output lines of the low energy detector and the high energy detector are connected with the data collector, and the data output lines of the data collector and the thickness measuring probing heads mounted on both sides of the conveying mechanism are all connected with the data processing computer.

In the above described apparatus, said low energy radiation source and high energy radiation source may be an X-ray machine or a linear electron accelerator, or an isotope having a single energy level.

The invention provides an apparatus for liquid safety-detection with a radiation source, the apparatus comprising a radiation shield, and a radiation source for emitting a ray beam, a shield type collimator, a conveying mechanism, thickness measuring probing heads, a post collimator and a detector, which are located in the radiation shield; and further comprising a data collector having an amplifying and forming circuit, and a data processing computer provided with a database having substance densities and atomic numbers of dangerous liquids and with a liquid energy spectrum analyzing software for carrying out an energy spectrum analysis of the ray beam emitted from the radiation and penetrated through a liquid article to be detected, which data collector and data processing computer are located outside of the radiation shield; wherein said radiation source is located in the shield type collimator, the shield type collimator may be located on one side of the conveying mechanism on which an article to be detected can be placed, on the other side of the conveying mechanism successively mounted are the post collimator and the detector, to make the ray beam emitted from the radiation source face the post collimator and the detector after passing through the shield type collimator, the data output line of the detector is connected with the data collector, and the data output lines of the data collector and the thickness measuring probing heads mounted on both sides of the conveying mechanism are all connected with the data processing computer.

The apparatus according to the invention is characterized by that said radiation source may be an isotope of a radiation source having either a single energy level or multiple energy levels and may be an X-ray machine or a linear electron accelerator as well.

The invention further provides an apparatus for liquid safety-detection with a radiation source, the apparatus comprising a radiation shield, and double radiation sources each for emitting a ray beam, shield type collimators, a conveying mechanism, thickness measuring probing heads, post collimators and detectors, which are located in the radiation shield; further comprising a data collector having an amplifying and forming circuit, and a data processing computer provided with a database having substance densities and atomic numbers of dangerous liquids and with a liquid energy spectrum analyzing software for carrying out an energy spectrum analysis of the ray beams emitted from the radiation sources and penetrated through a liquid article to be detected, which data collector and data processing computer are located outside of the radiation shield; wherein, said double radiation sources are composed of a low energy radiation source and a high energy radiation source which are respectively located in the shield type collimators, each shield type collimator is located on one side of the conveying mechanism on which an article to be detected can be placed, on the other side of the conveying mechanism successively mounted are the post collimators and a low energy detector, a high energy detector, to make the ray beam emitted from the low energy radiation source face the post collimator and the low energy detector after passing through the shield type collimator, and the ray beam emitted from the high energy radiation source face the post collimator and the high energy detector after passing through the shield type collimator, the data output wires of the low energy detector and the high energy detector are connected with the data collector, and the data output lines of the data collector and the thickness measuring probing heads mounted on both sides of the conveying mechanism are all connected with the data processing computer.

The apparatus according to the invention is characterized by that said low energy radiation source and high energy radiation source may be an X-ray machine or a linear electron accelerator, or an isotope having a single energy level.

A method for safety-detecting a liquid using the apparatus according to the invention comprises the main steps of:

a) conveying an article to be detected into an operation zone within the radiation shield by the conveying mechanism;

b) allowing a ray beam to be emitted from the radiation source located in the shield type collimator, to pass through the article to be detected, then to pass the post collimator, and to be received by the detector facing the ray beam;

c) transmitting a data of a signal of a received ray beam to the data collector by the detector;

d) amplifying and forming the data of the signal of the received ray beam and transmitting such data to the data processing computer by the data collector, and transmitting a data collected by the thickness measuring probing heads mounted on both sides of the conveying mechanism to the data processing computer by the same; and e) processing a data from the data collector and a data from the thickness measuring probing heads and accomplishing an energy spectrum analysis of the penetrated ray beam of the detected article to derive the liquid density and atomic number of the detected article, comparing a result with densities and atomic numbers of dangerous articles in a existing database, and then visually displays the detected information of the detected article, by the data processing computer.

A method for liquid safety-detection using the apparatus according to the invention comprises the following steps:

conveying an article to be detected by said conveying mechanism, into a path of a ray beam to be emitted from said low energy radiation source between said the low energy radiation source and said low energy detector;

allowing a ray beam to be emitted from the low energy radiation source located in the shield type collimator, to pass through the article to be detected, then to pass a post collimator, and to be received by said low energy detector facing the ray beam;

transmitting a data of a signal of a received ray beam to the data collector by the low energy detector;

conveying the article to be detected by said conveying mechanism, into a path of a ray beam to be emitted from said high energy radiation source between said the high energy radiation source and said high energy detector;

allowing a ray beam to be emitted from the high energy radiation source located in the shield type collimator, to pass through the article to be detected, then to pass a post collimator, and to be received by said high energy detector facing the ray beam;

transmitting a data of a signal of a received ray beam to the data collector, by the high energy detector;

after processing the datas of signals of the received ray beams from the low energy detector and the high energy detector, transmitting thus formed data to the data processing computer by the data collector, and transmitting, the thickness measuring probing heads located on both sides of the conveying mechanism, a data collected by them to the data processing computer; and processing the datas from the data collector and the thickness measuring probing heads and accomplishing an energy spectrum analysis of a penetrated ray beam of the detected article to derive a liquid density and an atomic number of the detected article, comparing a result with densities and atomic numbers of dangerous articles in a existing database, and then visually displaying a detected information of the detected article, by the data processing computer.

Since the invention uses the above described methods and structures, safety-detects a packaged liquid article by use of a radiation source, derives the density and atomic number information of the detected liquid article, and compares the result with the densities and atomic numbers of dangerous liquids in a database; it is judged whether the detected liquid is dangerous article or not. Comparing to the prior art, the invention is not subjected to the affection of the outside package of an article and has great anti-interference, and has the features of small volume, high accuracy of detection, easy shielding, and high use safety and reliability.

The invention is further illustrated hereinafter in conjunction with the accompanying drawings and the particular embodiment forms.

DETAILED DESCRIPTION OF THE PREFERRED EMBODIMENT

Embodiment 1

Figure 1:
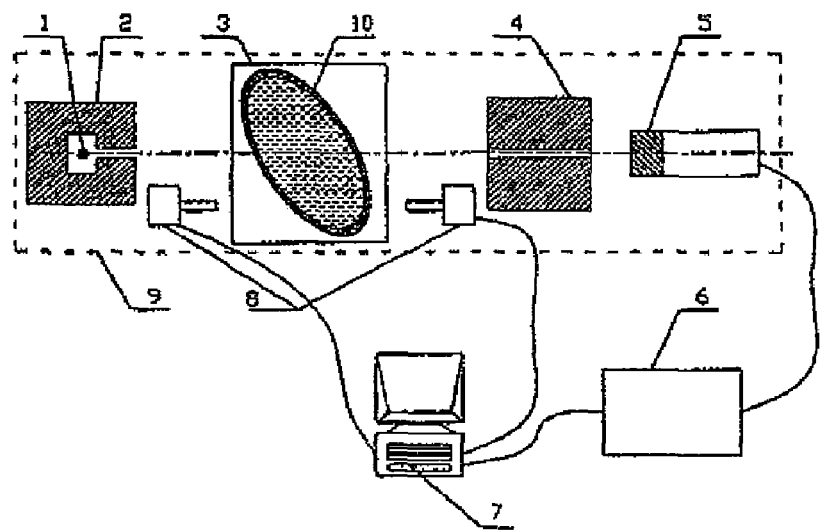
FIG. 1 is a schematic diagram of the structure of an embodiment form of an apparatus of the invention.

Referring to FIG. 1, an apparatus realizing a method of the invention comprises a radiation shield 9, and a radiation source 1, a shield type collimator 2, a conveying mechanism 3, thickness measuring probing heads 8, a post collimator 4 and a detector 5 which are located in the radiation shield 9. The apparatus further comprises a data collector 6 having an amplifying and forming circuit, and a data processing computer 7 provided with a database having substance densities and atomic numbers of dangerous articles and with an energy spectrum analyzing software for carrying out an energy spectrum analysis of penetrated ray beam of a liquid article to be detected, which are located outside of the radiation shield 9. In the apparatus, the radiation source 1 is an isotope having a single energy level or an X-ray machine, a rectilinear electron accelerator. The radiation source 1 is located in the shield type collimator 2, and the shield type collimator 2 is located on one side of the conveying mechanism 3 on which an article to be detected can be placed. On the other side of the conveying mechanism 3 successively mounted are the post collimator 4 and the detector 5, to make the ray beam emitted from the radiation source 1 face the post collimator 4 and the detector 5 after passing through the shield type collimator 2. The data output wire of the detector 5 is connected with the data collector 6, and the data output wires of the data collector 6 and the thickness measuring probing heads 8 mounted on both sides of the conveying mechanism 3 are all connected with the data processing computer 7.

The method, when used by the above described apparatus, comprises the steps of:

a) conveying a liquid article to be detected into an operation zone within the radiation shield 9 by the conveying mechanism 3;

b) allowing a ray beam to be emitted from the radiation source 1 located in the shield type collimator 2, to pass through the liquid article 10 to be detected, then to pass the post collimator 4, and to be received by the detector 5 facing the ray beam;

c) transmitting a data of a signal of a received ray beam to the data collector 6 by the detector 5;

d) amplifying and shaping the data of the signal of the received ray beam and transmitting the amplified and shaped data to the data processing computer by the data collector 6, and transmit a data, by the thickness measuring probing heads 8 mounted on both sides of the conveying mechanism 3, collected by them to the data processing computer 7;

e) processing a data from the data collector 6 and a data from the thickness measuring probing heads 8 and accomplishing an energy spectrum analysis of the penetrated ray beam of the detected liquid article 10 to derive a liquid density and an atomic number of the detected liquid article 10, comparing a result with densities and atomic numbers of dangerous articles in the existing database, and then visually displaying a detected information of the detected liquid article 10, by the data processing computer 7.

The present embodiment is suitable for the case in which the effective atomic number of the external package substance of the detected liquid article 10 is approximate to that of the liquid of the detected liquid article 10 or the external package is the known standard package and its effective atomic number has been recorded in the existing database.

Embodiment 2

The radiation source 1 in FIG. 1 is changed into an isotope with multiple energy levels. The structure of the apparatus and the steps of the method of the embodiment are same as those of Embodiment 1, and the description is not repeated.

The present embodiment is suitable for the examination and identification for liquids in the external packages of various standard or non-standard detected liquid articles 10.

Embodiment 3

Figure 2:
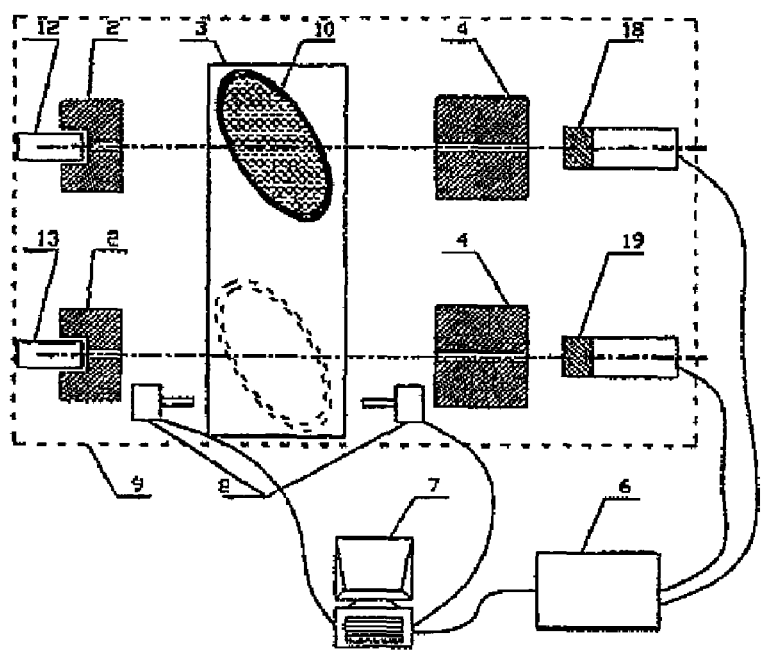
FIG. 2 is a schematic diagram of the structure of another embodiment form of an apparatus of the invention.
Figure 3:
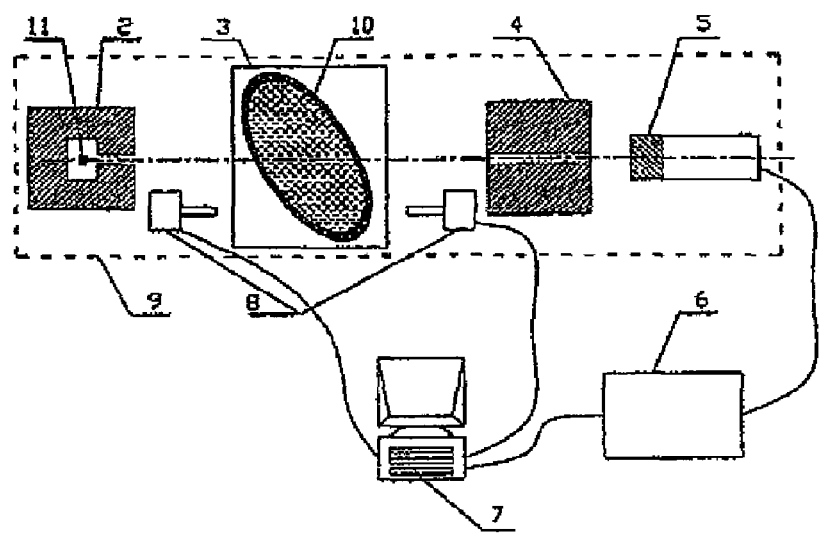
FIG. 3 is a schematic diagram of the structure of still another embodiment form of an apparatus of the invention, which differs from the embodiment in FIG. 1 only in that it has a rectilinear electron accelerator 11 as a specific form of the radiation source 1.
Figure 4:
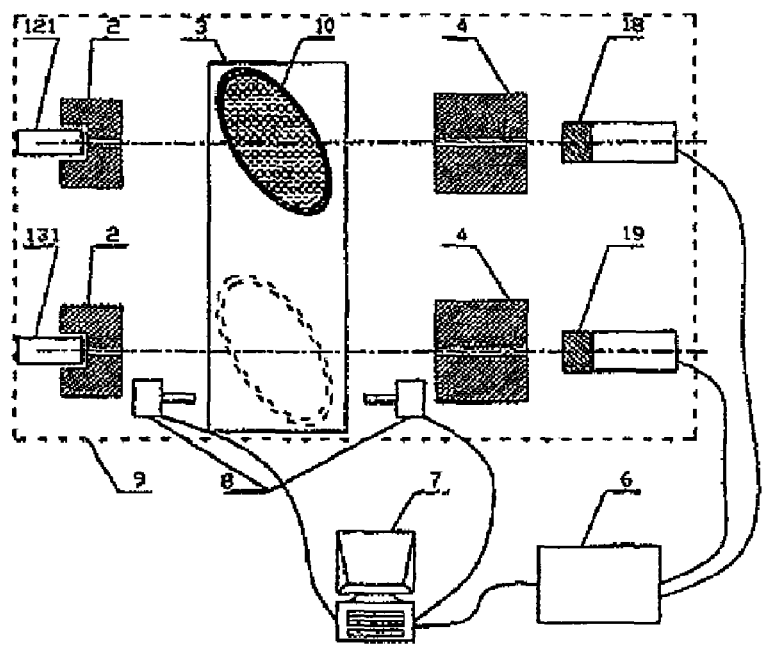
FIG. 4 is a schematic diagram of the structure of a further embodiment of the apparatus of the invention which is similar to the embodiment shown in FIG. 2 but differs from it in that this embodiment has two rectilinear electron accelerators 121 and 131 as a specific form of the radiation sources 12 and 13.

Referring to FIG. 2, FIG. 2 is another embodiment form of an apparatus of the invention, and it is a schematic diagram of the structure of the embodiment form using a double energy radiation source. The apparatus comprises a radiation shield 9, and double radiation sources, shield type collimators 2, a conveying mechanism 3, thickness measuring probing heads 8, post collimators 4 and detectors, which are located in the radiation shield 9. The apparatus further comprises a data collector 6 having an amplifying and forming circuit, and a data processing computer 7 provided with a database having substance densities and atomic numbers of dangerous articles and with an energy spectrum analyzing software for carrying out an energy spectrum analysis of a penetrated ray beam of a liquid article to be detected, which are located outside of the radiation shield 9. Said double radiation sources are composed of a low energy radiation source 12 and a high energy radiation source 13, which use an X-ray machine, a rectilinear electron accelerator or an isotope having a single energy level, and which are respectively located in the shield type collimators 2. Each shield type collimator 2 is located on one side of the conveying mechanism 3 on which an article to be detected can be placed, and on the other side of the conveying mechanism 3 successively mounted are the post collimators 4 and a low energy detector 18, a high energy detector 19, to make the ray beam emitted from the low energy radiation source 12 face the post collimator 4 and the low energy detector 18 after passing through the shield type collimator 2, and the ray beam emitted from the high energy radiation source 13 face the post collimator 4 and the high energy detector 19 after passing through the shield type collimator 2. The data output wires of the low energy detector 18 and the high energy detector 19 are connected with the data collector 6, and the data output lines of the data collector 6 and the thickness measuring probing heads 8 mounted on both sides of the conveying mechanism 3 are all connected with the data processing computer 7.

When the embodiment is used, a liquid article 10 to be detected is examined each time in accordance with the steps of the method of the above described Embodiment 1 respectively between the low energy radiation source 12 and the low energy detector 18 and the high energy radiation source 13 and the high energy detector 19. It is assured by the conveying mechanism 3 that two examinations of the detected liquid article 10 occur at the same position of the detected liquid article 10. The energy spectrum information of the low energy and high energy penetrating X-rays obtained respectively by the two examinations makes the detection more accurate, together with the thickness information of the ray passed through the detected liquid article 10.

Further it is illustrated that, exempt for the examination and identification of the detected liquid article 10, the above described various embodiment manners may also be used to make density examination and substance identification of other solid articles whose shapes are regular.

The invention claimed is:

1. A method for liquid safety-detection with a radiation source, comprising the use of the radiation source, a shield type collimator, a post collimator, a detector, a data collector, a data processing computer, thickness measuring probing heads and a radiation shield; and having the main steps of:
   a) conveying an article to be detected into an operation zone within the radiation shield by a conveying mechanism;
   b) allowing a ray beam to be emitted from the radiation source located in the shield type collimator, to pass through the article to be detected, then to pass said post collimator, and to be received by the detector facing the ray beam;
   c) transmitting a data of a signal of a received ray beam to the data collector, by the detector;
   d) amplifying and forming the data of the signal of the received ray beam and transmitting such data to the data processing computer by the data collector, and transmitting a data collected by the thickness measuring probing heads mounted on both sides of the conveying mechanism to the data processing computer by the same; and
   e) processing a data from the data collector and a data from the thickness measuring probing heads and accomplishing an energy spectrum analysis of a penetrated ray beam of the detected article to derive the liquid density and atomic number of the detected article, comparing a result with densities and atomic numbers of dangerous articles in a existing database, and then visually displaying a detected information of the detected article, by the data processing computer.

2. An apparatus for specially carrying out a the method for liquid safety-detection with a radiation source, comprising a radiation shield (9), and a radiation source (1) for emitting a ray beam, a shield type collimator (2), a conveying mechanism (3), thickness measuring probing heads (8), a post collimator (4) and a detector (5), which are located in the radiation shield (9); further comprising a data collector (6) having an amplifying and forming circuit, and a data processing computer (7) provided with a database having substance densities and atomic numbers of dangerous liquids and provided with a liquid energy spectrum analyzing software for carrying out an energy spectrum analysis of the ray beam emitted from the radiation source and penetrated through a liquid article to be detected, which data collector (6) and data processing computer (7) are located outside of the radiation shield (9); characterized by that said radiation source (1) is located in the shield type collimator (2), that the shield type collimator (2) is located on one side of the conveying mechanism (3) on which an article to be detected can be placed, that on the other side of the conveying mechanism (3) successively mounted are the post collimator (4) and the detector (5), to make the ray beam emitted from the radiation source (1) face the post collimator (4) and the detector (5) after passing through the shield type collimator (2), that a data output line of the detector (5) is connected with the data collector (6), and that data output lines of the data collector (6) and the thickness measuring probing heads (8) mounted on both sides of the conveying mechanism (3) are all connected with the data processing computer (7).

3. The apparatus according to claim 2, characterized by that said radiation source (1) is one of an isotope of a radiation source having either a single energy level or multiple energy levels, an X-ray machine and a rectilinear electron accelerator as well.

4. A method for safety-detecting a liquid, comprising the following steps:
conveying an article to be detected by a conveying mechanism, into a path of a ray beam to be emitted from a low energy radiation source (12) between said the low energy radiation source (12) and a low energy detector (18);
allowing a ray beam to be emitted from the low energy radiation source (12) located in a shield type collimator, to pass through the article to be detected, then to pass a post collimator, and to be received by said low energy detector (18) facing the ray beam;
transmitting a data of a signal of a received ray beam to a data collector (6), by the low energy detector;
conveying the article to be detected by said conveying mechanism, into a path of a ray beam to be emitted from a high energy radiation source (13) between said the high energy radiation source (13) and a high energy detector (19);
allowing a ray beam to be emitted from the high energy radiation source (13) located in a shield type collimator, to pass through the article to be detected, then to pass a post collimator, and to be received by said high energy detector (19) facing the ray beam;
transmitting data of a signal of a received ray beam to the data collector (6), by the high energy detector;
after processing the datas of signals of the received ray beams from the low energy detector and the high energy detector, transmitting thus formed data to a data processing computer by the data collector, and transmitting, by thickness measuring probing heads located on both sides of the conveying mechanism, a data collected by them to the data processing computer; and
processing the datas from the data collector and the thickness measuring probing heads and accomplishing an energy spectrum analysis of a penetrated ray beam of the detected article to derive a liquid density and an atomic number of the detected article, comparing a result with densities and atomic numbers of dangerous articles in a existing database, and then visually displaying a detected information of the detected article, by the data processing computer.

5. An apparatus for specially carrying out a method for liquid safety-detection with a radiation source, comprising a radiation shield (9), and double radiation sources each for emitting a ray beam, shield type collimators (2), a conveying mechanism (3), thickness measuring probing heads (8), post collimators (4), a high energy detector, and a low energy detector which are located in the radiation shield (9); further comprising a data collector (6) having an amplifying and forming circuit, and a data processing computer (7) provided with a database having substance densities and atomic numbers of dangerous liquids and with a liquid energy spectrum analyzing software for carrying out an energy spectrum analysis of the ray beams emitted from the radiation source and penetrated through a liquid article to be detected, which data collector (6) and data processing computer (7) are located outside of the radiation shield (9), characterized by that said double radiation sources are composed of a low energy radiation source (12) and a high energy radiation source (13) which are respectively located in one of the shield type collimators (2), that each shield type collimator (2) is located on one side of the conveying mechanism (3) on which an article to be detected can be placed, that on the other side of the conveying mechanism (3) successively mounted are the post collimators (4) and the low energy detector (18), the high energy detector (19), to make the ray beam emitted from the low energy radiation source (12) face the post collimator (4) and the low energy detector (18) after passing through the shield type collimator (2), and the ray beam emitted from the high energy radiation source (13) face the post collimator (4) and the high energy detector (19) after passing through the shield type collimator (2), that data output wires of the low energy detector (18) and the high energy detector (19) are connected with the data collector (6), and that data output lines of the data collector (6) and the thickness measuring probing heads (8) mounted on both sides of the conveying mechanism (3) are all connected with the data processing computer (7).

6. The apparatus according to claim 5, characterized by that said low energy radiation source (12) and high energy radiation source (13) are one of an X-ray machine, a rectilinear electron accelerator, and an isotope having a single energy level.

* * * * *